United States Patent
Li et al.

(10) Patent No.: US 9,549,712 B2
(45) Date of Patent: Jan. 24, 2017

(54) METHOD AND APPARATUS FOR CORRECTING FOCUS OF CT DEVICE

(71) Applicant: Shenyang Neusoft Medical Systems Co., Ltd., Shenyang (CN)

(72) Inventors: Shuangxue Li, Shenyang (CN); Xin Xiang, Shenyang (CN); Zhewen Jiang, Shenyang (CN)

(73) Assignee: SHENYANG NEUSOFT MEDICAL SYSTEMS CO., LTD., Shenyang ( * ) Notice: Subject to any disclaimer, the term of this patent is extended or adjusted under 35 U.S.C. 154(b) by 337 days.

(21) Appl. No.: 14/477,862

(22) Filed: Sep. 5, 2014

(65) Prior Publication Data

US 2015/0117618 A1 Apr. 30, 2015

(30) Foreign Application Priority Data

Oct. 30, 2013 (CN) .......................... 2013 1 0532861

(51) Int. Cl.
*A61B 6/00* (2006.01)
*A61B 6/03* (2006.01)

(52) U.S. Cl.
CPC ............... *A61B 6/586* (2013.01); *A61B 6/405* (2013.01); *A61B 6/4021* (2013.01); *A61B 6/54* (2013.01); *A61B 6/032* (2013.01)

(58) Field of Classification Search
CPC ......... A61B 6/032; A61B 6/035; A61B 6/402; A61B 6/405; A61B 6/5258; A61B 6/54; H05G 1/36; H05G 1/52; H05G 1/54; H01J 35/02; H01J 35/10; H01J 35/14; H01J 35/305
See application file for complete search history.

(56) References Cited

U.S. PATENT DOCUMENTS

| | | | |
|---|---|---|---|
| 4,991,189 A | 2/1991 | Boomgaarden et al. | |
| 5,835,559 A | 11/1998 | Hsieh | |
| 6,094,469 A * | 7/2000 | Dobbs | A61B 6/583 378/19 |
| 6,980,623 B2 * | 12/2005 | Dunham | A61B 6/06 378/136 |
| 8,331,529 B2 * | 12/2012 | Miller | A61B 6/032 378/147 |

(Continued)

FOREIGN PATENT DOCUMENTS

| | | |
|---|---|---|
| CN | 1191710 A | 9/1998 |
| CN | 101900823 A | 12/2010 |

(Continued)

*Primary Examiner* — Thomas R Artman
(74) *Attorney, Agent, or Firm* — Kilpatrick Townsend & Stockton LLP

(57) ABSTRACT

A method and apparatus for correcting a focus of a CT device are provided. The method includes: calculating a total focus shift according to scanning data; and correcting, when the CT device is running, a deflection of an electron beam emitted from a ray source of the CT device, based on the total focus shift. The device includes: a shift calculation module, configured to calculate a total focus shift according to scanning data; and a shift correction module, configured to correct, when the CT device is running, a deflection of an electron beam emitted from a ray source of the CT device, based on the total focus shift.

18 Claims, 6 Drawing Sheets

(56) References Cited

U.S. PATENT DOCUMENTS

| | | | |
|---|---|---|---|
| 8,971,480 B2* | 3/2015 | Hockersmith | G01N 23/046 378/15 |
| 2005/0094762 A1* | 5/2005 | Dunham | A61B 6/06 378/19 |
| 2010/0020938 A1* | 1/2010 | Koch | H05G 1/52 378/138 |
| 2010/0119039 A1* | 5/2010 | Miller | A61B 6/032 378/62 |
| 2014/0362969 A1* | 12/2014 | Hockersmith | G01N 23/046 378/4 |
| 2015/0117618 A1* | 4/2015 | Li | A61B 6/586 378/207 |

FOREIGN PATENT DOCUMENTS

| | | |
|---|---|---|
| CN | 102770077 A | 11/2012 |
| CN | 103140172 A | 6/2013 |
| JP | 2000033085 A | 2/2000 |
| JP | 2007014608 A | 1/2007 |

\* cited by examiner

METHOD AND APPARATUS FOR CORRECTING FOCUS OF CT DEVICE

The present application claims the priority to Chinese Patent Application No. 201310532861.X, entitled "METHOD AND APPARATUS FOR CORRECTING FOCUS OF CT DEVICE", filed on Oct. 30, 2013 with the State Intellectual Property Office of People's Republic of China, which is incorporated herein by reference in its entirety.

FIELD OF TECHNOLOGY

The present disclosure relates to the technical field of optical scanning, and in particular to a method and apparatus for correcting a focus of a CT device.

BACKGROUND

A Computed Tomography (CT) device (a short for computer tomography scanning system) is a common instrument for medical imaging diagnosis. Simply speaking, the CT device is to perform tomography scanning with X rays.

A structure and principle for a CT device is as follows. A tube is used as a ray source, an electron beam, generated from a cathode of the tube under an effect of a high voltage filament, shoots at an anode target to be refracted as rays in a fan geometry, and then scanning and imaging are performed by using the rays to implement imaging diagnosis, as shown in FIG. 1.

Due to a high requirement on accuracy of a medical CT device, control for rays in the CT device is extremely rigorous. Focus position of the rays is critical for controlling the direction and angle of the rays. The so-called focus refers to a point where the electron beam is refracted on the anode target. The focus may be considered as a source of the rays, and the accuracy of the focus position is the basis for achieving accurate control of the rays. Once the focus position has an error, the direction and the angle of the rays may be significantly affected.

Unfortunately, the generation and control of rays in the tube of the conventional CT device generally depend on mechanical components to some extent, and therefore the derived mechanical error is unavoidable. In practical application, when the angle of the rays is changed, a rotation of the anode target, a rotation of a gantry, cold shrinkage and thermal expansion of the anode target may affect the focus position. As shown by the dashed lines in FIG. 1, as the anode target and the gantry rotate, the anode target shifts to the position represented by the dashed line due to an effect of gravity; and the focus and the rays are also shifted due to the shift of the anode target. Referring to the X-Y-Z spatial coordinate system shown in FIG. 1, the rays shift in X-axis and Z-axis respectively.

In conventional technology, correction of shift in focus position is normally confined in a mechanical level. For example, by providing a ray detector to detect the change in radiation position of the rays on the detector and by adjusting related mechanical components accordingly, a constant radiation position on the detector is ensured and a correction for the position is achieved. However, such a conventional mechanical method, naturally subjected to a restriction of mechanical movement, is hard to realize quick correction in real time and has a relative slow adjustment speed; and hardware modification in connection with the mechanical method brings relatively high cost.

SUMMARY

In view of this, the disclosure is to provide a method and apparatus for correcting a focus of a CT device. In the method, a focus shift under an error condition is calculated in advance, and then rays are corrected based on the focus shift in an information processing manner.

Accordingly, technical solutions are provided in the disclosure as follows.

A method for correcting a focus of a CT device, includes:
calculating a total focus shift according to scanning data; and correcting, when the CT device is running, a deflection of an electron beam emitted from a ray source of the CT device, based on the total focus shift.

The scanning data includes a rotation angle of a gantry, a rotation angle of an anode target and a heat storage of the anode target. The process of calculating the total focus shift according to scanning data includes:
calculating a first focus shift according to the rotation angle of the gantry, calculating a second focus shift according to the rotation angle of the anode target, and calculating a third focus shift according to the heat storage of the anode target; and
calculating the total focus shift by superposing the first focus shift, the second focus shift and the third focus shift.

Specifically, the process of calculating the first focus shift according to the rotation angle of the gantry includes:
extracting continuous rotation angels of the gantry generated from the running of the CT device in advance, and establishing a first shift model for the continuous rotation angles of the gantry and focus shifts corresponding to the gantry rotations according to a geometrical principle; and
acquiring, when the CT device is running, a current rotation angle of the gantry, and calculating the first focus shift according to the current rotation angle of the gantry by using the first shift model.

Specifically, the process of calculating the second focus shift according to the rotation angle of the anode target includes:
extracting continuous rotation angels of the anode target generated from the running of the CT device in advance, and establishing a second shift model for the continuous rotation angles of the anode target and focus shifts corresponding to the anode target rotations according to a geometrical principle; and
acquiring, when the CT device is running, a current rotation angle of the anode target, and calculating the second focus shift according to the current rotation angle of the anode target by using the second shift model.

Specifically, the process of calculating the third focus shift according to the heat storage of the anode target includes:
extracting continuous thermal capacities of the anode target generated from the running of the CT device in advance, and establishing a third shift model for the continuous thermal capacities of the anode target and focus shifts corresponding to the thermal capacities of the anode target according to a geometrical principle; and
acquiring, when the CT device is running, a current heat storage of the anode target, and calculating the third focus shift according to the current heat storage of the anode target by using the third shift model.

The focus shift includes: a horizontal shift of the focus and a vertical shift of the focus.

Specifically, the process of correcting the deflection of the electron beam emitted from the ray source based on the total focus shift includes:

correcting, by the ray source, the deflection of an initial direction of the emitted electron beam based on deflection compensation data for the electron beam, wherein the deflection compensation data is calculated by substituting the total focus shift into a transfer function.

An apparatus for correcting a focus of a CT device, includes:

a shift calculation module, configured to a total focus shift according to scanning data; and a shift correction module, configured to correct, when the CT device is running, a deflection of an electron beam emitted from a ray source of the CT device, based on the total focus shift.

The scanning data includes a rotation angle of a gantry, a rotation angle of an anode target and a heat storage of the anode target. The shift calculating module includes:

a first calculating unit, configured to calculate a first focus shift according to the rotation angle of the gantry;

a second calculating unit, configured to calculate a second focus shift according to the rotation angle of the anode target;

a third calculating unit, configured to calculate a third focus shift according to the heat storage of the anode target; and a superposing unit, configured to calculate the total focus shift by superposing the first focus shift, the second focus shift and the third focus shift.

The shift correction module includes:

a transfer unit, configured to substitute the total focus shift into a transfer function to calculate deflection compensation data for the electron beam; and a correcting unit, configured to correct, via the ray source, the deflection of an initial direction of the emitted electron beam based on the deflection compensation data.

It may be known from the above solutions that the disclosure is advantageous as follows: no additional operation in connection with mechanical components is brought to the CT device and no restriction due to the mechanical movement is suffered; the correction for the focus position through information processing is relatively faster, and requirement of real time performance may be met; with such a method, there is no need to modify the structure of the CT device, which avoids an increased cost for a hardware modification; in addition, focus shift is calculated in advance, the total focus shift is calculated quickly when the CT device is running by using mathematic modeling, and the real-time performance and accuracy for correcting and adjusting focus position are further improved.

BRIEF DESCRIPTION OF THE DRAWINGS

To describe the technical solutions according to the embodiments of the present disclosure or conventional technology more clearly, in the following the drawings involved in the embodiments of the present disclosure or in the conventional technology are described. Apparently, the drawings described below are only some of the embodiments, and persons of ordinary skill in the art can derive other drawings according to the drawings without any creative effort.

DETAILED DESCRIPTION OF THE EMBODIMENTS

To make the objectives, technical solutions, and merits of the present disclosure clearer, the technical solution in the embodiments of the application will be clearly and completely described hereinafter in conjunction with drawings. Apparently, the embodiments described are merely a few embodiments of the application, rather than all embodiments. Any other embodiments obtained based on the embodiments in the disclosure by those skilled in the art without any creative works should fall within the scope of protection of the application.

In the disclosure, a focus position of the CT device is not corrected through a mechanical method, but in the following way: calculating a focus shift under a mechanical error and correcting an angle at which a ray source emits an electron beam based on the focus shift, so as to ensure that the electron beam may be refracted on a constant position of an anode target, and a constant focus of the rays is ensured.

Figure 2:
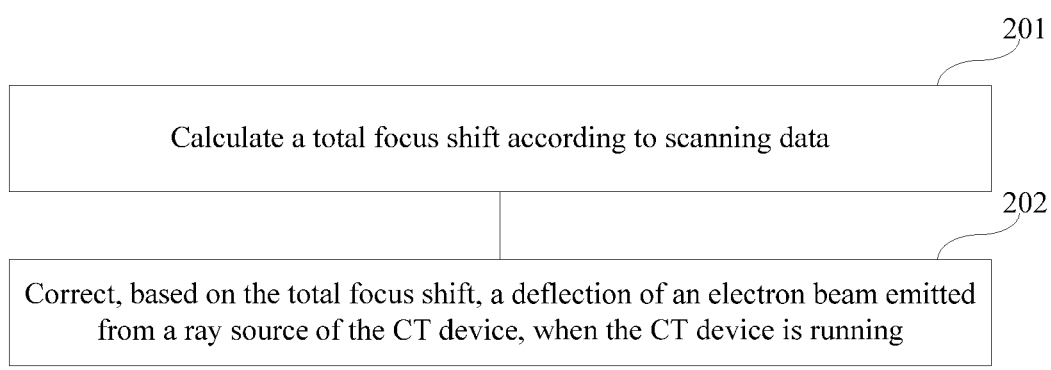
FIG. 2 is a flowchart diagram of the method according to an embodiment of the disclosure.

FIG. 2 illustrates a method for correcting a focus of a CT device in an embodiment of the disclosure. The method in the embodiment includes following steps.

Step 201 is to calculate a total focus shift according to scanning data.

The scanning data refer to parameter values that produce regular mechanical error and affect a focus position when the CT device is running. In the embodiment, the scanning data includes a rotation angle of a gantry, a rotation angle of an anode target and a heat storage of the anode target.

The gantry and the anode target both have regular axis rotation when the CT device is running. In the rotation, affected by objective factors such as gravity and slight irregularity of bearings, the position of the anode target may have errors changing regularly as the gantry or the anode target rotates, and accordingly the focus position is affected. Heat storage of the anode target reflects situation of cold shrinkage and thermal expansion for the anode target. As the heat storage changes, the volume and shape of the anode target may change according to a rule and accordingly the focus position is affected.

Each of the three kinds of scanning data in the embodiment affects the focus position independently by following a determined rule. Therefore, focus shift incurred by each kind of scanning data may be calculated respectively. In other words, a first focus shift is calculated according to the rotation angle of the gantry, a second focus shift is calculated according to the rotation angle of the anode target, and a third focus shift is calculated according the heat storage of the anode target. The total focus shift is calculated by superposing the first focus shift, the second focus shift and the third focus shift. Specific manner for calculating the focus shift is not limited herein.

It should be noted that the terms of total focus shift, first focus shift, second focus shift and third focus shift are all sub-concepts of focus shift. For convenience of calculation and subsequent processing, the focus shift is divided into two components in mathematics, namely a horizontal shift and a vertical shift of the focus. Referring to a reference coordinate system of FIG. 1, the horizontal shift refers to the focus shift on X-axis, and the vertical shift refers to the focus shift on Y-axis.

Step 202 is to correct, based on the total focus shift, a deflection of an electron beam emitted from a ray source, when the CT device is running.

In this embodiment, the correction of a focus position is implemented by adjusting the ray source. The ray source may be a tube in the CT device. In the step, an angel and a direction of the electron beam emitted by the tube are compensated according to the value of the total focus shift, to ensure that the electron beam always shoots at a fixed position on the anode target as a position of the anode target changes, which implements the correction of the focus position.

The specific way for correcting the deflection of the electron beam emitted from the ray source according to the total focus shift may include: substituting the total focus shift into a transfer function to calculate deflection compensate data for the electron beam, and correcting, via the ray source, the deflection of an initial direction of the emitted electron beam based on the deflection compensation data. This is an information processing process, in which the total focus shift may be converted to the deflection compensation data through the transfer function, and the deflection compensation data may represent an angle for correcting the deflection of the electron beam. Then the deflection correction of the electron beam emitted by the ray source may be achieved according to the deflection compensate data.

It may be seen that in the embodiment, the correction of the focus position is achieved by correcting, based on the total focus shift, the angle for the ray source to emit the electron beam. The embodiment is advantageous in that: no additional operation in connection with mechanical components is brought to the CT device and no restriction due to the mechanical movement is suffered; the correction of the focus position through information processing is relatively faster, and requirement of real time performance may be met; with such a method, there is no need to modify the structure of the CT device, which avoids an increased cost for a hardware modification.

Figure 3:
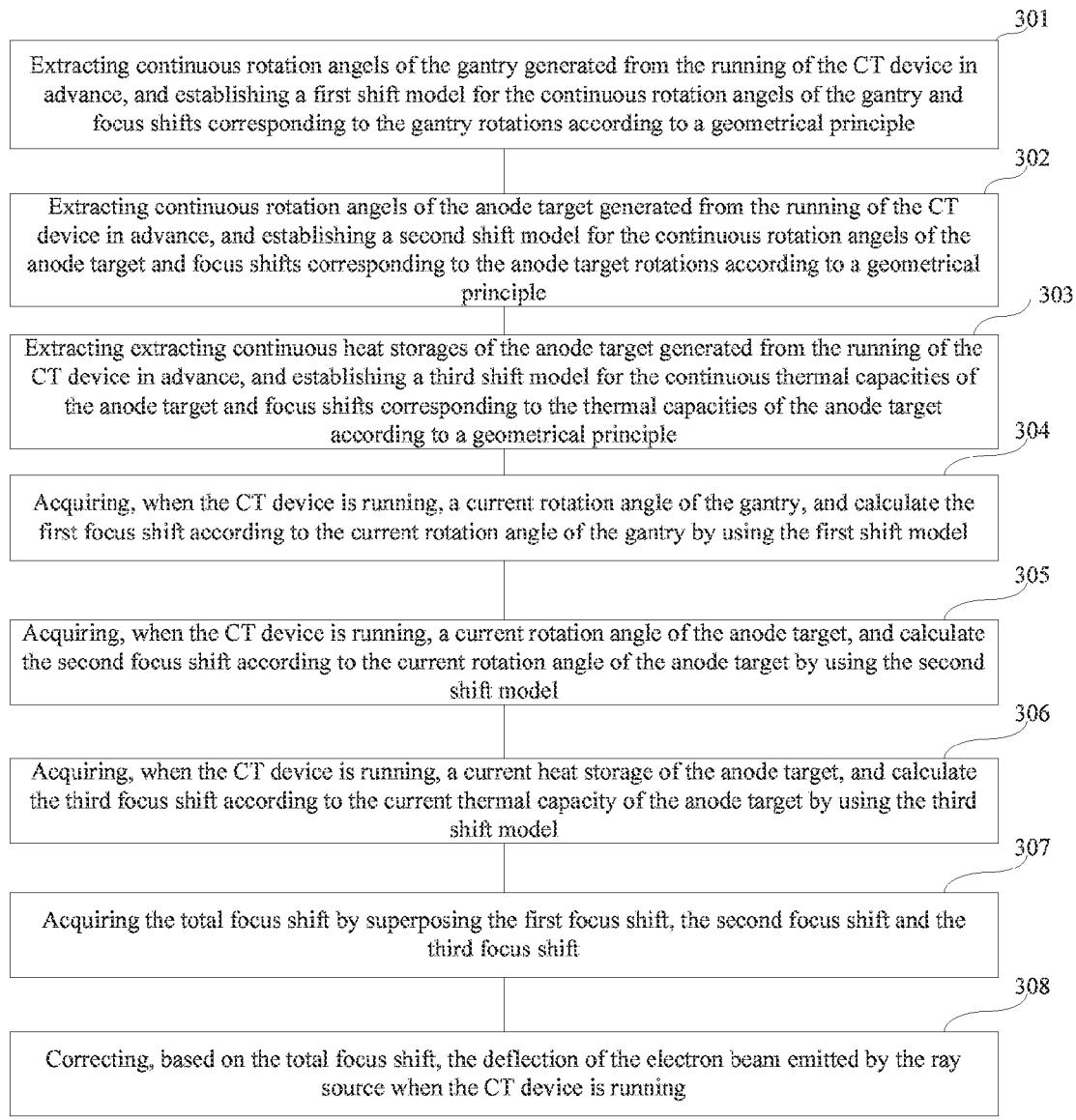
FIG. 3 is a flowchart diagram of the method according to another embodiment of the disclosure.

FIG. 3 illustrates a method for correcting a focus of a CT device according to another embodiment of the disclosure. This embodiment emphasizes calculation of the focus shift according to the scanning data, on the basis of the embodiment of the FIG. 2. The method according to this embodiment includes following steps.

Step 301 may include extracting continuous rotation angels of the gantry generated from the running of the CT device in advance, and establishing a first shift model for the continuous rotation angels of the gantry and focus shifts corresponding to the gantry rotations according to a geometrical principle.

Step 302 may include extracting continuous rotation angels of the anode target generated from the running of the CT device in advance, and establishing a second shift model for the continuous rotation angels of the anode target and focus shifts corresponding to the anode target rotations according to a geometrical principle.

Step 303 may include extracting continuous thermal capacities of the anode target generated from the running of the CT device in advance, and establishing a third shift model for the continuous thermal capacities of the anode target and focus shifts corresponding to the thermal capacities of the anode target according to a geometrical principle.

In the embodiment, in order to further improve efficiency for focus correction, focus shift is calculated in advance rather than being calculated when the CT device is running; and based on the calculated results acquired in advance together with mathematic modeling, the total focus shift is calculated quickly when the CT device is running.

The scanning data in the embodiment also includes the rotation angle of the gantry, the rotation angle of the anode target and the heat storage of the anode target. Step 301 to step 303 are processes for calculation performed according to the three kinds of scanning data respectively. Different kinds of scanning data result in focus shifts independently, so for a calculation according to one kind of scanning data, only the focus shift generated under an effect of this kind of scanning data, which is also called a focus shift corresponding to this kind of scanning data, is considered.

It is known that the rotation angle, the temperature or the heat storage are continuously variable data. In other words, the scanning data has the characteristics of varying continuously with time when the CT device is running; the scanning data affect the focus position by following a certain rule. It may be considered that if one kind of the scanning data is taken as a variable, correspondingly generated focus shift of the scanning data may be taken as a function of the variable.

Principles for calculating focus shifts respectively according to the three kinds of scanning data are basically the same, so only the case in connection with the rotation angle of the gantry is taken as an example to illustrate herein, other cases following the same principle are not described herein.

Continuous rotation angels of the gantry generated from running of the CT device, which may range from 0 to 360 degrees, are extracted in advance, i.e., one cycle of continuous rotation by the gantry is taken as scanning data. Every single rotation angle during the cycle of rotation by the gantry may affect the position of the anode target to different extent and a specific focus shift may be generated. That's to say, any rotation angle of the gantry has one corresponding focus shift in connection with the gantry rotation.

Focus shift at a specific angle may be calculated based on a geometrical principle. A special geometric algorithm is described in the embodiment, as shown in FIG. 4.

Figure 1:
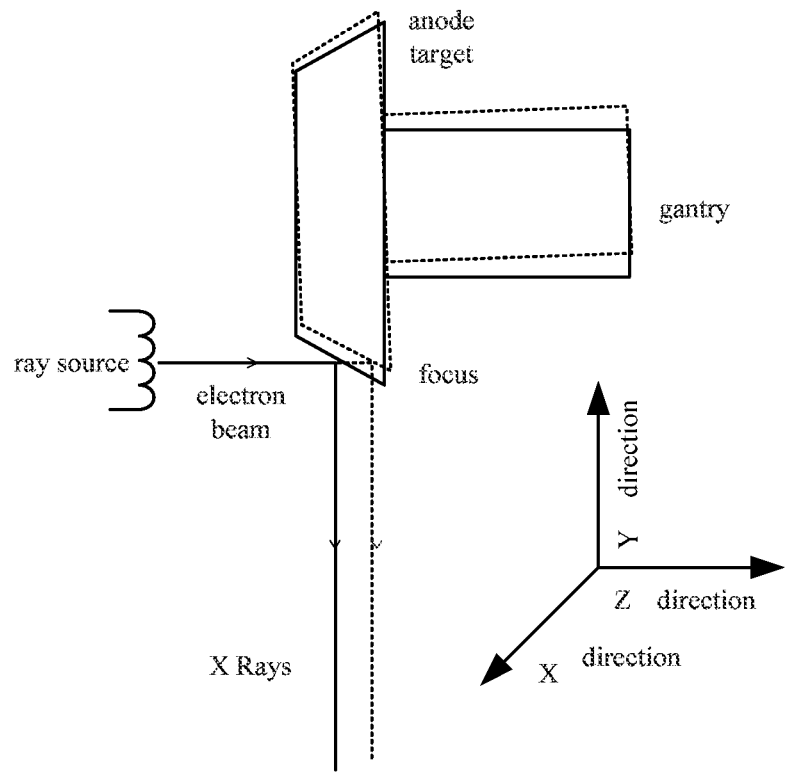
FIG. 1 is a structural schematic diagram of a conventional CT device.
Figure 4:
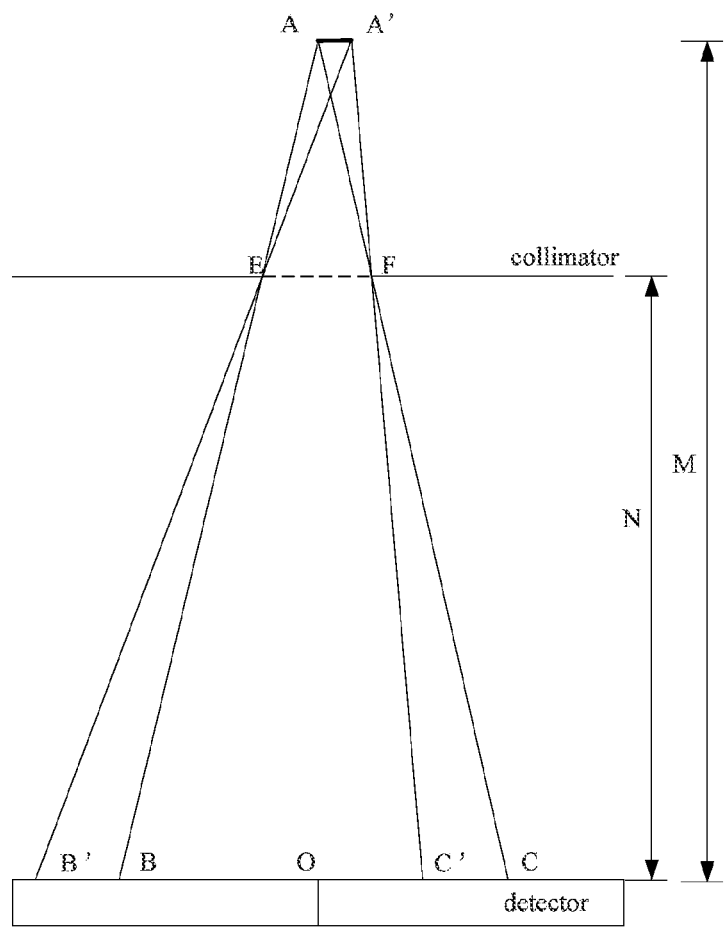
FIG. 4 is a schematic diagram of a geometric relation for shifted positions of the focus.

In the existing CT device, rays shown in FIG. 1 may enter into a collimator and a detector shown in FIG. 4. In FIG. 4, a space between points E and F represents a slit of the collimator; point A represents a theoretical focus position, the distance BC represents a theoretical range that the rays cover the detector, point A' represents a shifted focus position, the distance B'C' represents a range that the rays actually cover the detector after the shift; a vertical distance between the focus and the detector is indicated by M, and a vertical distance between the slit of the collimator and the detector is indicated by N; in the existing CT device, the above listed parameters are measurable; and the distance AA' represents the focus shift.

Actual distance of AA' may be calculated according to geometrical relationship between above determined parameters in the formula as follows:

Supposing that O is a center point of the detector, distances BO, CO, B'O, C'O may be measured by the detector. If $$\frac{B'O}{C'O} = K; \text{ then } AA' = \frac{K-1}{K+1} \cdot \frac{EF}{2} \cdot \frac{M}{N}$$

Figure 5:
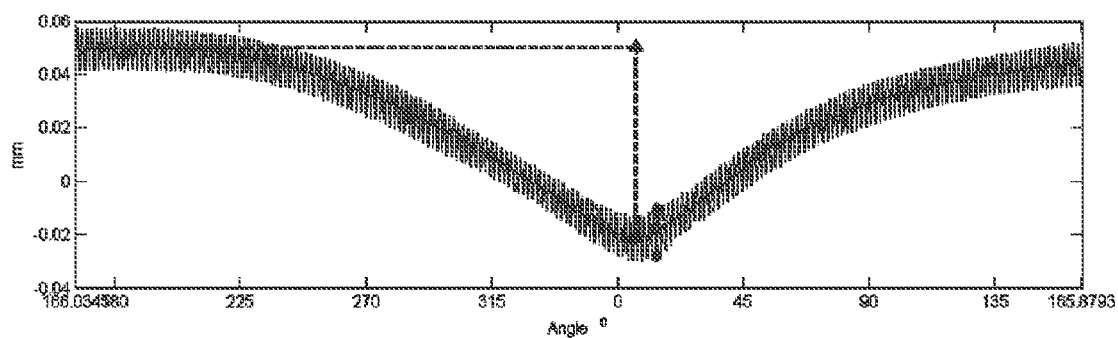
FIGS. 5-6 are graphs showing a functional curve for a rotation angle of a gantry and corresponding focus shift.
Figure 6:
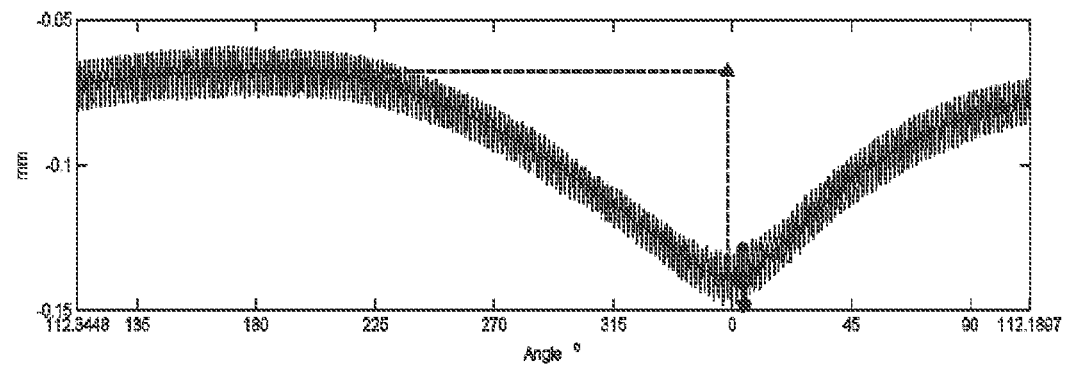

The above algorithm is extended to calculate continuous focus shifts correspondingly generated from continuous rotation angles of the gantry, and a functional curve for rotation angle of the gantry and corresponding focus shift may be plotted, as shown in FIGS. 5-6. FIG. 5 reflects horizontal shift in the focus shift corresponding to the gantry rotation, and FIG. 6 reflects vertical shift in the focus shift corresponding to the gantry rotation. In FIGS. 5-6, the abscissa represents the rotation angle of the gantry, and the ordinate represents the value of the shift.

Figure 7:
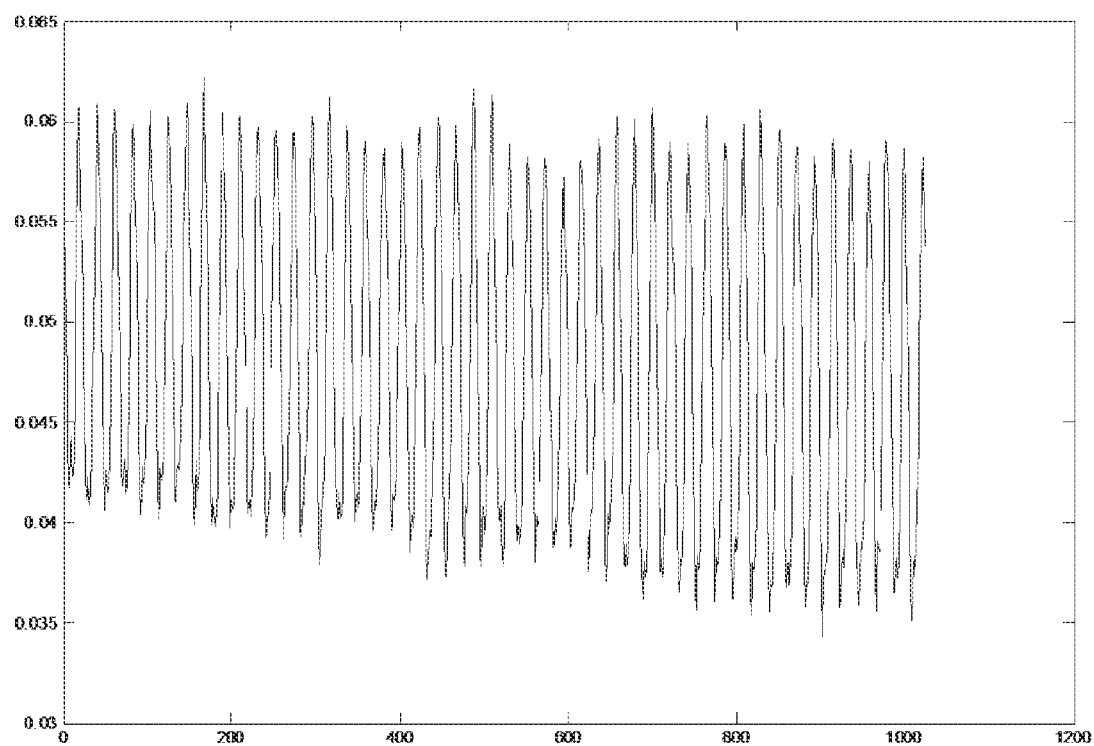
FIGS. 7-8 are graphs showing a functional curve for a rotation angle of an anode target and corresponding focus shift.
Figure 8:
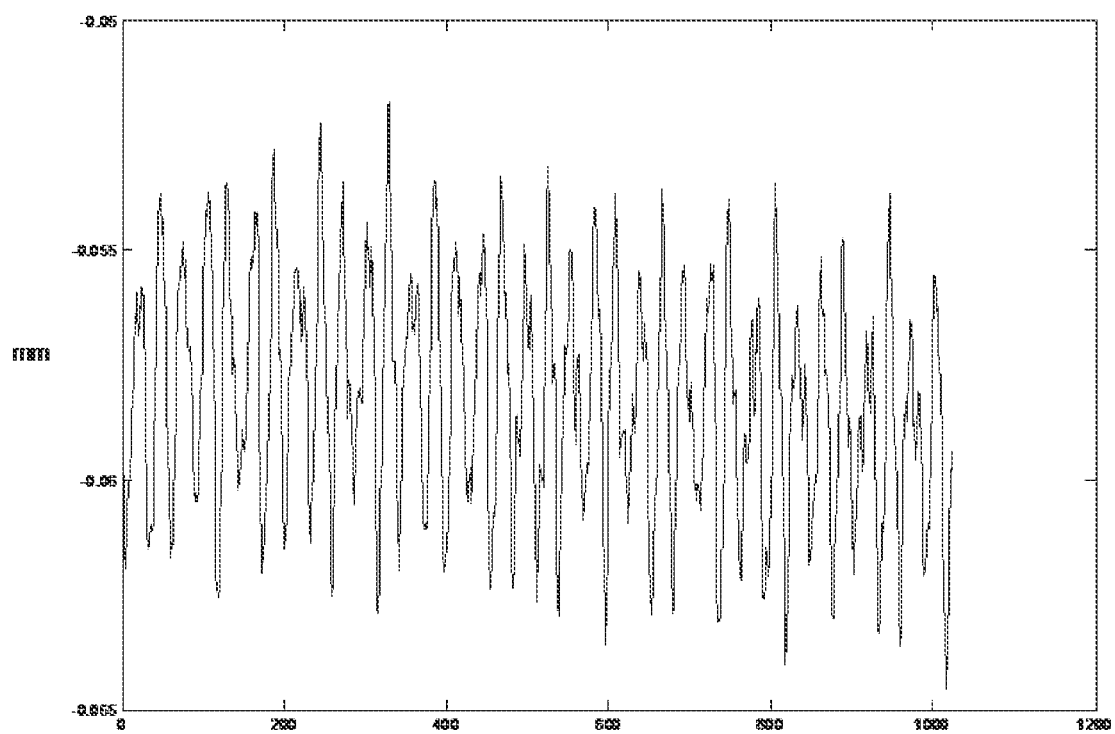

In the same way, FIGS. 7-8 are functional curves for the rotation angle of the anode target and corresponding focus shift, where FIG. 7 reflects horizontal shift in the focus shift corresponding to the anode target rotation, and FIG. 8 reflects vertical shift in the focus shift corresponding to the anode target rotation. It should be noted that, ordinate of FIGS. 7-8 represents the value of the shift and abscissa represents a parameter about the rotation angle of the anode target in the desirable unit "view" derived from an integration for the rotation angle of the anode target and time. The unit view is commonly known in the art and is not described in detail herein.

Figure 9:
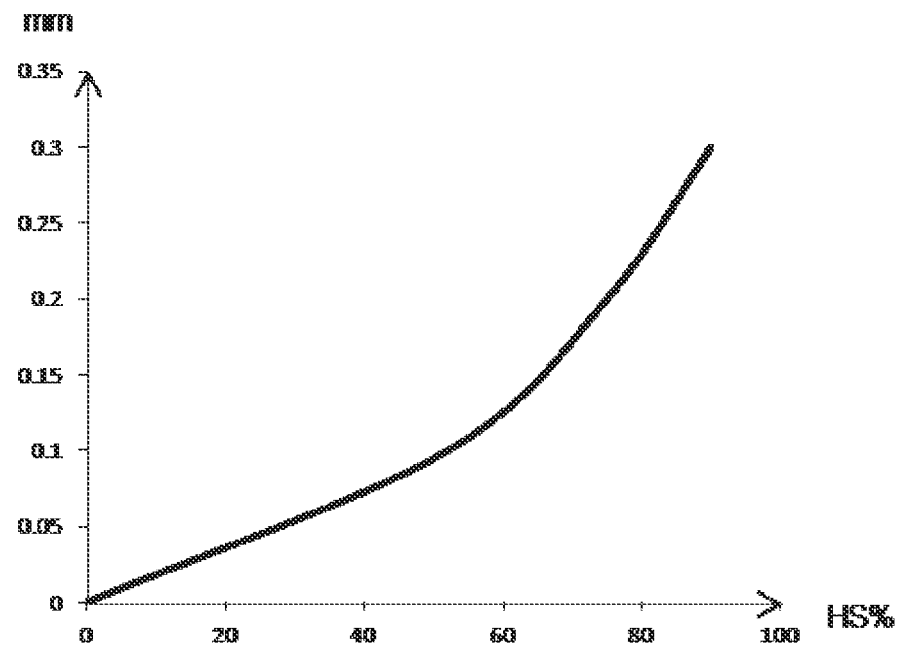
FIG. 9 is a graph showing a functional curve for a heat storage of an anode target and corresponding focus shift.

FIG. 9 is a functional curve for thermal expansion of the anode target and the vertical shift in the corresponding focus shift. Since the focus shift corresponding to thermal expansion of the anode target is mainly shown as the vertical shift, the horizontal shift is negligible. In FIG. 9, abscissa represents heat storage in percentage, and ordinate represents the value of the shift.

In the embodiment, the functional relationships shown in FIGS. 5-9 are further taken as mathematic models. FIGS. 5-6 reflect a first shift model, FIGS. 7-8 reflect a second shift model, and FIG. 9 reflects a third shift model. The three models fully correspond to the three kinds of scanning data. Obviously, when a CT device is running, a focus shift generated by one specific kind of scanning data may be acquired through substituting the scanning data into a corresponding shift model.

Step 304 is to acquire, when the CT device is running, a current rotation angle of the gantry, and calculate the first focus shift according to the current rotation angle of the gantry by using the first shift model.

Step 305 is to acquire, when the CT device is running, a current rotation angle of the anode target, and calculate the second focus shift according to the current rotation angle of the anode target by using the second shift model.

Step 306 is to acquire, when the CT device is running, a current heat storage of the anode target, and calculate the third focus shift according to the current heat storage of the anode target by using the third shift model.

Step 304-step 306 are processes for calculating actual focus shifts according to shift models. In the embodiment, shift models are established in advance before the CT device runs, so when the CT device runs to function, every kind of scanning data at a current moment may be acquired in real time and substituted into a corresponding shift model, so as to quickly acquire the first focus shift, the second focus shift and the third focus shift at the current moment.

Step 307 is to acquire the total focus shift by superposing the first focus shift, the second focus shift and the third focus shift.

Step 308 is to correct, based on the total focus shift, the deflection of the electron beam emitted by the ray source when the CT device is running.

In the embodiment, due to the simplified calculation process of the total focus shift and the good real-time performance of each of the first focus shift, the second focus shift, the third focus shift and the total focus shift, the embodiment is advantageous in that: the focus shift is calculated in advance, and the total focus shift is calculated quickly when the CT device is actually running according to the focus shift together with the mathematical modeling, therefore a real-time performance and accuracy for correcting and adjusting the focus position are further improved. In addition, the technical solution of the method in the embodiment is more complete with the detailed disclosure.

Figure 10:
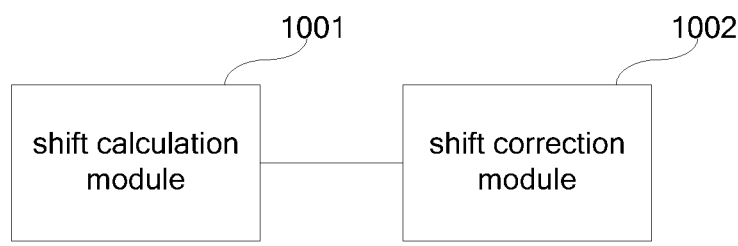
FIG. 10 is a structural schematic diagram of the apparatus according to an embodiment of the disclosure.

Corresponding to an embodiment of the method shown in FIG. 2, the disclosure further provides an apparatus for correcting a focus of a CT device to implement the method. The apparatus has substantially same essence as the method shown in FIG. 2 and of the description in connection with the embodiment shown in FIG. 2 is similarly applicable for this embodiment. With reference to FIG. 10, the apparatus includes the following elements.

The apparatus includes a shift calculation module 1001, configured to calculate a total focus shift according to scanning data.

The scanning data includes a rotation angle of a gantry, a rotation angle of an anode target and a heat storage of the anode target. The shift calculation module includes:

a first calculating unit, configured to calculate a first focus shift according to the rotation angle of the gantry;

a second calculating unit, configured to calculate a second focus shift according to the rotation angle of an anode target;

a third calculating unit, configured to calculate a third focus shift according to the heat storage of the anode target; and a superposing unit, configured to calculate the total focus shift by superposing the first focus shift, the second focus shift and the third focus shift.

The apparatus includes a shift correction module 1002, configured to correct, when the CT device is running, a deflection of an electron beam emitted by a ray source, based on the total focus shift.

The shift correction module may include a transfer unit, configured to substitute the total focus shift into a transfer function to calculate deflection compensation data for the electron beam; and a correcting unit, configured to correct, via the ray source, the deflection of an initial direction of the emitted electron beam, based on the deflection compensation data.

It may be known from the above solution that the device in the present embodiment is advantageous in that: no additional operation in connection with mechanical components is brought to the CT device and no restriction due to the mechanical movement is suffered; the correction for the focus position through information processing is relatively faster, and requirement of real time performance may be met; with such a method, there is no need to modify the structure of the CT device, which avoids an increased cost for a hardware modification.

The foregoing are preferred embodiments of the disclosure. It should be noted that for persons of ordinary skills in the art some modifications and improvements may be made within the principle of the disclosure; these modifications and improvements fall within the scope of the claims.

The invention claimed is:

1. A method for correcting a focus of a CT device, comprising:

calculating a total focus shift according to scanning data; and correcting, when the CT device is running, a deflection of an electron beam emitted from a ray source of the CT device, based on the total focus shift; wherein the scanning data comprises a rotation angle of a gantry, a rotation angle of an anode target and a heat storage of the anode target.

2. The method according to claim 1, wherein the process of correcting the deflection of the electron beam emitted from the ray source of the CT device comprises correcting an angle at which the electron beam is emitted from the ray source.

3. The method according to claim 1, wherein the process of calculating the total focus shift according to the scanning data comprises:
    calculating a first focus shift according to the rotation angle of the gantry, calculating a second focus shift according to the rotation angle of the anode target, and calculating a third focus shift according to the heat storage of the anode target; and
    calculating the total focus shift by superposing the first focus shift, the second focus shift and the third focus shift.

4. The method according to claim 3, wherein the process of calculating the first focus shift according to the rotation angle of the gantry comprises:
    extracting continuous rotation angels of the gantry generated from the running of the CT device in advance, and establishing a first shift model for the continuous rotation angles of the gantry and focus shifts corresponding to the gantry rotations according to a geometrical principle; and
    acquiring, when the CT device is running, a current rotation angle of the gantry, and calculating the first focus shift according to the current rotation angle of the gantry by using the first shift model.

5. The method according to claim 3, wherein the process of calculating the second focus shift according to the rotation angle of the anode target comprises:
    extracting continuous rotation angels of the anode target generated from the running of the CT device in advance, and establishing a second shift model for the continuous rotation angels of the anode target and focus shifts corresponding to the anode target rotations according to a geometrical principle; and
    acquiring, when the CT device is running, a current rotation angle of the anode target, and calculating the second focus shift according to the current rotation angle of the anode target by using the second shift model.

6. The method according to claim 3, wherein the process of calculating the third focus shift according to the heat storage of the anode target comprises:
    extracting continuous thermal capacities of the anode target generated from the running of the CT device in advance, and establishing a third shift model for the continuous thermal capacities of the anode target and focus shifts corresponding to the thermal capacities of the anode target according to a geometrical principle; and
    acquiring, when the CT device is running, a current heat storage of the anode target, and calculating the third focus shift according to the current heat storage of the anode target by using the third shift model.

7. The method according to claim 1, wherein the focus shift comprises: a horizontal shift of the focus and a vertical shift of the focus.

8. The method according to claim 2, wherein the process of correcting the angle at which the electron beam is emitted from the ray source comprises:
    correcting, by the ray source, the deflection of an initial direction of the emitted electron beam based on deflection compensation data for the electron beam, wherein the deflection compensation data is calculated by substituting the total focus shift into a transfer function.

9. The method according to claim 1, wherein the process of correcting the deflection of the electron beam emitted from the ray source of the CT device comprises correcting an angle at which the electron beam is emitted from the ray source by:
    correcting, by the ray source, the deflection of an initial direction of the emitted electron beam based on deflection compensation data for the electron beam, wherein the deflection compensation data is calculated by substituting the total focus shift into a transfer function.

10. An apparatus for correcting a focus of a CT device, wherein the apparatus comprises:
    a shift calculation module, configured to calculate a total focus shift according to scanning data; and
    a shift correction module, configured to correct, when the CT device is running, a deflection of an electron beam emitted from a ray source of the CT device, based on the total focus shift; wherein the scanning data comprises a rotation angle of a gantry, a rotation angle of an anode target and a heat storage of the anode target.

11. The apparatus according to claim 10, wherein the shift correction module is further configured to correct, based on the total focus shift, an angle at which the electron beam is emitted from the ray source to correct the deflection of the electrical beam emitted from the ray source of the CT device.

12. The apparatus according to claim 10, wherein the shift calculating module comprises:
    a first calculating unit, configured to calculate a first focus shift according to the rotation angle of the gantry;
    a second calculating unit, configured to calculate a second focus shift according to the rotation angle of the anode target;
    a third calculating unit, configured to calculating a third focus shift according to the heat storage of the anode target; and
    a superposing unit, configured to calculate the total focus shift by superposing the first focus shift, the second focus shift and the third focus shift.

13. The apparatus according to claim 12, wherein the first calculating unit is further configured for:
    extracting continuous rotation angels of the gantry generated from the running of the CT device in advance, and establishing a first shift model for the continuous rotation angles of the gantry and focus shifts corresponding to the gantry rotations according to a geometrical principle; and
    acquiring, when the CT device is running, a current rotation angle of the gantry, and calculating the first focus shift according to the current rotation angle of the gantry by using the first shift model.

14. The apparatus according to claim 12, wherein the second calculating unit is further configured for:
    extracting continuous rotation angels of the anode target generated from the running of the CT device in advance, and establishing a second shift model for the continuous rotation angels of the anode target and focus shifts corresponding to the anode target rotations according to a geometrical principle; and
    acquiring, when the CT device is running, a current rotation angle of the anode target, and calculating the second focus shift according to the current rotation angle of the anode target by using the second shift model.

15. The apparatus according to claim 12, wherein the third calculating unit is further configured for:
   extracting continuous thermal capacities of the anode target generated from the running of the CT device in advance, and establishing a third shift model for the continuous thermal capacities of the anode target and focus shifts corresponding to the thermal capacities of the anode target according to a geometrical principle; and
   acquiring, when the CT device is running, a current heat storage of the anode target, and calculating the third focus shift according to the current heat storage of the anode target by using the third shift model.

16. The apparatus according to claim 10, wherein the shift correction module comprises:
   a transfer unit, configured to substitute the total focus shift into a transfer function to calculate deflection compensation data for the electron beam; and
   a correcting unit, configured to correct, via the ray source, the deflection of an initial direction of the emitted electron beam, based on the deflection compensation data.

17. The apparatus according to claim 10, wherein the focus shift comprises: a horizontal shift of the focus and a vertical shift of the focus.

18. The apparatus according to claim 10, wherein the shift correction module is further configured to correct, based on the total focus shift, an angle at which the electron beam is emitted from the ray source to correct the deflection of the electrical beam emitted from the ray source of the CT device by:
   correcting, by the ray source, the deflection of an initial direction of the emitted electron beam based on deflection compensation data for the electron beam, wherein the deflection compensation data is calculated by substituting the total focus shift into a transfer function.

* * * * *